(12) United States Patent
Plevin et al.

(10) Patent No.: US 9,784,744 B2
(45) Date of Patent: Oct. 10, 2017

(54) LABELED CHIRAL ALPHA-HYDROXY KETOACID DERIVATIVES, A PROCESS FOR PREPARING SAID DERIVATIVES AND THEIR USE

(71) Applicants: COMMISSARIAT A L'ENERGIE ATOMIQUE ET AUX ENERGIES ALTERNATIVES, Paris (FR); Centre National de la Recherche Scientifique, Paris (FR)

(72) Inventors: Michael Plevin, Grenoble (FR); Rime Kerfah, Fontaine (FR); Ombeline Pessey, Fontaine (FR); Jérôme Boisbouvier, Saint Vincent de Mercuze (FR); Pierre Gans, Voreppe (FR)

(73) Assignees: Commissariat a l'Energie Atomique et aux Energies Alternatives, Paris (FR); Centre National de la Recherch Scientifique, Paris (FR)

( * ) Notice: Subject to any disclaimer, the term of this patent is extended or adjusted under 35 U.S.C. 154(b) by 114 days.

(21) Appl. No.: 14/419,759

(22) PCT Filed: Aug. 7, 2013

(86) PCT No.: PCT/IB2013/056468
§ 371 (c)(1),
(2) Date: Feb. 5, 2015

(87) PCT Pub. No.: WO2014/024151
PCT Pub. Date: Feb. 13, 2014

(65) Prior Publication Data
US 2015/0212093 A1    Jul. 30, 2015

(30) Foreign Application Priority Data
Aug. 8, 2012   (EP) .................................. 12305984

(51) Int. Cl.
*G01N 33/58*     (2006.01)
*C07C 59/215*    (2006.01)
(Continued)

(52) U.S. Cl.
CPC .......... *G01N 33/58* (2013.01); *C07B 59/001* (2013.01); *C07C 59/215* (2013.01); *C07K 1/13* (2013.01);
(Continued)

(58) Field of Classification Search
CPC ............... G01N 33/58; G01N 33/6812; G01N 2458/15; C07K 1/13; C07B 59/001; C07C 59/215; C12P 7/42; C12P 21/02
(Continued)

(56) References Cited

U.S. PATENT DOCUMENTS

2006/0148042 A1   7/2006  Chipman et al.
2013/0122598 A1*  5/2013  Gans et al. .................... 436/86

FOREIGN PATENT DOCUMENTS

WO   WO 03/062436 A1   7/2003
WO   WO 2011/083356   7/2011

OTHER PUBLICATIONS

Ayala I et al.; Chem. Comm.; 2011.
(Continued)

*Primary Examiner* — Brian J Sines
(74) *Attorney, Agent, or Firm* — Alston & Bird LLP (57) ABSTRACT

The present invention relates to labeled chiral alpha-hydroxy ketoacid derivatives, a process for preparing the derivatives and their use for isotopic labeling of amino acids, in particular, for isotopic labeling of methyl groups of amino acids, and more particularly, for specific isotopic labeling of valine, leucine and isoleucine methyl groups, in proteins and biomolecular assemblies. The invention also concerns a process for analyzing proteins and biomolecular assemblies (Continued)

by NMR spectroscopy including a step of isotopic labeling of amino acids, in particular, valine, leucine and isoleucine, in proteins and biomolecular assemblies to be analyzed by the chiral alpha-hydroxy ketoacid derivatives of the invention.

The invention further relates to a kit for isotopic labeling of valine, leucine and isoleucine amino acids, in proteins and biomolecular assemblies including one or more chiral alpha-hydroxy ketoacid derivatives of the invention.

6 Claims, 9 Drawing Sheets

(51) Int. Cl.
    *C07B 59/00*     (2006.01)
    *C12P 21/02*     (2006.01)
    *C07K 1/13*     (2006.01)
    *C12P 7/42*     (2006.01)
    *G01N 33/68*     (2006.01)

(52) U.S. Cl.
    CPC ............... *C12P 7/42* (2013.01); *C12P 21/02* (2013.01); *G01N 33/6812* (2013.01); *G01N 2458/15* (2013.01)

(58) Field of Classification Search
    USPC ...................................... 436/86, 90
    See application file for complete search history.

(56) References Cited

OTHER PUBLICATIONS

Ruschak A.M. et al.; J. Biomol NMR; 2010; 48(3); p. 129-35.
Ayala I. et al.; J. Chem. Comm.; 2012; 48(10); p. 1434-1436.
Godoy-Ruiz R. et al.; J. Am. Chem. Soc.; 2010; 132(51); p. 18340-50.
Engel, S. et al.; Biotechnology & Bioengineering; 88; p. 825-83.
Bar-Ilan et al.; Biochemistry 40 (2001) 11946-54.
Hill et al.; Biochem. J.; 1997.
Biotechnol Bioeng; 2004; 88(7); 825-31.
P. Gans et al.; Angew. Chem. Int. Ed.; 2010; 49; pp. 1958-1962.
International Search Report and Written Opinion for International Application No. PCT/IB2013/056468 dated Dec. 17, 2013.
David H. G. Crout et al.; J.C.S. Perkin I (1979); p. 1982-1989.
By D. J. Robins et al.; J. Chem Soc.; (1970); 1334-1336.
Hill et al.; Bioorganic Chemistry; 8, (1979); p. 175-189.
Armstrong et al.; J. Chem. Soc.; (1983); I; p. 1197-1201.

* cited by examiner

LABELED CHIRAL ALPHA-HYDROXY KETOACID DERIVATIVES, A PROCESS FOR PREPARING SAID DERIVATIVES AND THEIR USE

FIELD

The present invention relates to labeled chiral alpha-hydroxy ketoacid derivatives, a process for preparing said derivatives and their use for isotopic labeling of amino acids, in particular, for isotopic labeling of methyl groups of amino acids, and more particularly, for specific isotopic labeling of valine, leucine and isoleucine methyl groups, in proteins and biomolecular assemblies.

The invention also concerns a process for analyzing proteins and biomolecular assemblies by NMR spectroscopy comprising a step of isotopic labeling of amino acids, in particular, valine, leucine and isoleucine, in proteins and biomolecular assemblies to be analyzed by the chiral alpha-hydroxy ketoacid derivatives of the invention.

The invention further relates to a kit for isotopic labeling of valine, leucine and isoleucine amino acids, in proteins and biomolecular assemblies, comprising one or more chiral alpha-hydroxy ketoacid derivatives of the invention.

BACKGROUND

The use of solution NMR spectroscopy to analyze the dynamics, interactions and function of large proteins (>100 kDa) and supra-molecular systems is becoming increasingly feasible. Key to this advance has been the development of new and powerful ways of labeling biomolecules has been critical for stimulating many of the advances in NMR methodology.

Methyl groups have been proven to be ideal molecular probes for solution NMR spectroscopy studies of large proteins.

In initial methyl-labeling procedures, alpha-keto acids were used as precursors in the production of methyl-protonated isoleucine (Ile). A more recent strategy is based on the use of labelled 2-(S)-2-hydroxy-2-ethyl-3-oxobutanoate, a biosynthetic precursor of isoleucine in *E. Coli* (Ayala I. et al., Chem Comm., 2011, www.rsc.org/chemcomm, DOI: 10.1039/C1CC12932E). In this method, the precursor is chemically synthetized meaning that the precursor is obtained as a racemic mixture and that only half of the mixture obtained can be converted by the bacteria.

Valine (Val), leucine (Leu) and isoleucine (Ile) are three amino acids of great interest as their methyl groups account for more than 50% of all methyl probes available in proteins.

Protonation of leucine and valine methyl groups in per-deuterated proteins is commonly achieved using methyl protonated 2-oxo-3-methylbutanoic acid (also known as alpha-ketoisovalerate), an intermediate in the biosynthesis of these amino acids, in which both methyl groups are $^1$H, $^{13}$C-labeled. The use of this type of alpha-ketoisovalerate proved inefficient in high-molecular-weight proteins as it results in overcrowded [$^1$H,$^{13}$C]-correlated spectra due to the sheer number of NMR-visible methyl probes.

WO 2011/083356 describes a process for the specific isotopic labeling of Valine (Val), leucine (Leu) and isoleucine (Ile) in protein assemblies using a racemic mixture of acetolactate derivatives obtained by chemical synthesis. Resolution of said racemic mixtures into their stereochemically pure acetolactate derivatives by conventional methods proved ineffective.

Ruschak A. M. et al., J Biomol NMR, 2010, 48(3), p. 129-35 and Ayala I. et al., J. Chem Commun, 2012, 48, p. 1434-1436 describe synthetic routes for preparing ester derivatives of 2-hydroxy-2-methyl-3-oxobutanoic acid and 2-hydroxy-2-ethyl-3-oxobutanoate for the specific labeling of Isoleucine gamma-2 methyl groups. In these references, the compounds are prepared by chemical synthesis from methyl (or ethyl) acetoacetate and are thus obtained in the form of a racemic mixture. Consequently, only half of the compound obtained with the S stereochemistry—can be incorporated by the bacteria. Moreover, the derivatives of 2-hydroxy-2-methyl-3-oxobutanoic acid and 2-hydroxy-2-ethyl-3-oxobutanoate are in the form of an ester, meaning that an additional step is required to deprotect the compounds in basic medium before use. Under poorly controlled reaction conditions, this may result in a significant degradation of the compounds.

Godoy-Ruiz R. et al., J. Am. Chem. Soc., 2010, 132(51), p. 18340-50 describe simultaneous selective isotope labeling of Alanine, Leucine, Valine and Isoleucine methyl positions using alpha-ketoisovalerate (for labeling Ala, Leu and Val sites) and alpha-ketobutyrate (for labeling of Ile positions) and their use to obtain distance restraints and mobility data. The labeling method described in this reference leads to isotopic leaks in the gamma-2 position of Isoleucines resulting in artifacts in the extraction of structural constraints. This phenomenon is due to the deamination of some of the labeled 3-$^{13}$C-alanine leading to the in viva synthesis of labeled pyruvate. The condensation of the thus obtained labeled pyruvate with endogenous 2-oxobutanoate in the presence of the acetolactate synthase, yields 2-hydroxy-2-ethyl-3-oxo-4-$^{13}$C-butanoate.

Engel, S. et al., Biotechnology & Bioengineering, 88, p. 825-83, reports the use of acetohydroxyacid synthase I (AHAS I) from *Escherichia Coli* in the stereoselective synthesis of aromatic alpha-hydroxy ketones.

US 2006/0148042 relates to a biotransfounation process for the preparation of chiral aromatic alpha-hydroxy ketones using acetohydroxyacid synthase (AHAS) or tartronate semialdehyde synthase (TSAS). This document is totally silent regarding the synthesis of non aromatic synthesis of chiral acetohydroxy acids, the synthesis of chiral acetohydroxy acids specifically or entirely deuterated and/or enriched in carbon 13 ($^{13}$C) and their use for isotopic labeling of amino acids.

Thus, there remains a need for labeled stereospecific alpha-hydroxyl ketoacids that are capable of efficiently and specifically label amino acids, in particular the methyl groups of amino acids selected from leucine, valine and isoleucine.

In particular, there remains a need for labeled stereospecific alpha-hydroxy ketoacids as described above, that are manufactured by a regioselective and stereospecific process in high yields and under mild conditions.

More particularly, there remains a need for labeled stereospecific alpha-hydroxy ketoacids as described above, capable of labeling the amino acid without causing isotopic leaks at the site where the amino acid is labeled, i.e. the methyl group of amino acids leucine, valine and isoleucine.

Even more particularly, there remains a need for labeled stereospecific alpha-hydroxy ketoacids as described above, that can be incorporated into the target protein by the bacteria without detectable scrambling.

SUMMARY

The present invention addresses these and other needs in the art by providing a compound of formula (I) having an (S) configuration:

(I)

wherein
- $X^1$ and $X^2$ are, independently from each other, $^1H$ (H) or $^2H$ (D);
- $Y^1$, $Y^2$ and $Y^3$ are, independently from each other, $^{12}C$ (C) or $^{13}C$;
- $R^1$ is a methyl group in which the carbon atom is $^{12}C$ (C) or $^{13}C$ and the hydrogen atoms are, independently from each other, $^1H$ (H) or $^2H$ (D);
- $R^2$ is a methyl group in which the carbon atom is $^{12}C$ (C) or $^{13}C$ and the hydrogen atoms are, independently from each other, $^1H$ (H) or $^2H$ (D); or
- $R^2$ is an ethyl group in which the carbon atoms are, independently from each other, $^{12}C$ (C) or $^{13}C$ and the hydrogen atoms are, independently from each other, $^1H$ (H) or $^2H$ (D), with the proviso that in compound of formula (I), at the same time, at least one hydrogen atom is $^2H$ (D) and at least one carbon atom is $^{13}C$.

Compounds of formula (I) having an (S) configuration, are also known as 2-(S)-alpha-acetolactic acid derivatives or 2-(S)-2-hydroxy-2-alkyl-3-oxobutanoic acid derivatives.

The compounds of formula (I) are chiral. The stereogenic/chiral center in the compounds of the invention, which is either a $^{12}C$ (C) or a $^{13}C$, has an (S) configuration. Consequently, the amount of the compounds of formula (I) required for isotopically labeling amino acids in a protein, is reduced by half, in comparison to the amount of the racemic mixtures of the art needed for the same operation.

Another advantage of the compounds of the invention is that unlike the ester compounds of the art, the compounds of formula (I) are in the form of an acid, thus avoiding the additional deprotection step of the ester function, which may be experimentally difficult.

A further advantage of the compounds of the invention is that with the compounds of formula (I), a high level of isotopic labeling of amino acids is obtained without any leakage towards the other positions.

In the context of the present invention, the following terms have the following meanings:
- Val designates amino acid valine;
- Leu designates amino acid leucine;
- Ile designates amino acid isoleucine;
- $^{13}C$ designates the carbon-13 isotope;
- $^{12}C$ (or C) designates the carbon-12 isotope;
- $^2H$ (or D) designates the isotope of hydrogen which is known as deuterium;
- $^1H$ (or H) designates the common isotope of hydrogen;
- chiral molecule is a molecule that has a non-superposable mirror image, the property of rotating the plane of polarization of plane-polarized monochromatic light that is passed through it. In the present invention, the chiral/stereogenic center is the carbon atom ($^{13}C$ or $^{12}C$) in compounds of formula (I) which bears four different substituent group, i.e. the carbon at position 2;
- configuration designates the spatial arrangement of the atoms directly attached to a stereogenic/chiral center in a chiral molecule. This arrangement is assigned in the chemical formula with the letter (R) or (S). In the present case compounds of formula (I) have an (S) configuration;
- biomolecular assemblies designate molecules containing proteins and other groups such as DNA loops (structures where the two strands of a double-stranded DNA molecule are separated for a stretch and held apart by a third strand of DNA), lipids, various ligands, etc;
- stereospecificity designates marked specificity for one of several stereoisomers of a substrate or reactant; usually is said of enzymes or of organic reactions;
- regio selectivity designates one direction of bond making or breaking preferentially over all other possible directions;
- proR, proS: the methyl groups (delta 1 and delta 2) on the gamma carbon of unlabeled Leu are not different and consequently the said gamma carbon of unlabeled Leu aminoacid is not chiral. The methyl groups (gamma 1 and gamma 2) on the beta carbon of unlabeled Val are not different and consequently the said beta carbon of unlabeled Val amino acid is not chiral.

However, when the groups $R^1$ and $R^2$ are not labeled in the same manner in the compounds of formula (I), the resulting methyl groups on the gamma and beta carbon atoms of, respectively, Leu and Val are differently labeled. Due to this difference, the gamma and beta carbon atoms of, respectively, Leu and Val become chiral. These methyl groups are designated as proR when labeling gives rise to an (R) configuration and as proS when labeling gives rise to an (S) configuration.

In a preferred embodiment, in the compound of formula (I) having an (S) configuration:
- $X^1$, $X^2$, $Y^1$, $Y^2$ and $Y^3$ are as previously defined;
- $R^1$ is chosen from a group consisting of $CD_3$, $^{13}CH_3$, $^{13}CH_2D$ and $^{13}CHD_2$,
- $R^2$ is a methyl group chosen from a group consisting of $^{13}CD_3$; or
- $R^2$ is an ethyl group chosen from a group consisting of $CD_3\text{-}CD_2$, $^{13}CH_3\text{-}CD_2$, $^{13}CHD_2\text{-}CD_2$, $^{13}CHD_2\text{-}^{13}CD_2$, $^{13}CH_2D\text{-}CD_2$, $^{13}CH_2D\text{-}^{13}CD_2$ and $^{13}CH_3\text{—}^{13}CD_2$.

In another preferred embodiment, in the compound of formula (I) having an (S) configuration:
- $X^1$, $X^2$, $R^1$ and $R^2$ are as previously defined in the various embodiments; and
- $Y^1\!=\!Y^2\!=\!Y^3\!=\!C$.

In a still another preferred embodiment, in the compound of formula (I) having an (S) configuration:
- $X^1$, $X^2$, $R^1$ and $R^2$ are as previously defined in the various embodiments; and
- $Y^1\!=\!Y^2\!=\!Y^3\!=\!{}^{13}C$.

In an embodiment of this invention, compound of formula (I) having an (S) configuration is chosen from the group consisting of:
- (S)-2-(1'-$^2H_2$, 2'-$^{13}C$)ethyl-2-hydroxy-3-oxo-4-($^2H_3$) butanoic acid $\{X^1\!=\!X^2\!=\!H; Y^1\!=\!Y^2\!=\!Y^3\!=\!C; R^1\!=\!CD_3; R^2\!=\!{}^{13}CH_3\text{—}CD_2\}$;
- (S)-2-(1'-$^2H_2$, 2'-$^2H$, 2'-$^{13}C$)ethyl-2-hydroxy-3-oxo-4-($^2H_3$)butanoic acid $\{X^1\!=\!X^2\!=\!H; Y^1\!=\!Y^2\!=\!Y^3\!=\!C; R^1 CD_3; R^2\!=\!{}^{13}CH_2\_D\_CD_2\}$;
- (S)-2-(1'-$^2H_2$, 2'-$^2H_2$, 2'-$^{13}C$,)ethyl-2-hydroxy-3-oxo-4-($^2H_3$)butanoic acid $\{X^1\!=\!X^2\!=\!H; Y^1\!=\!Y^2\!=\!Y^3\!=\!C; R^1\!=\!CD_3; R^2\!=\!{}^{13}CHD_2\_CD_2\}$;
- (S)-2-hydroxy-2-($^2H_3$,$^{13}C$)methyl-3-oxo-4($^{13}C$)butanoic acid $\{X^1\!=\!X^2\!=\!H; Y^1\!=\!Y^2\!=\!Y^3\!=\!C; R^1\!=\!{}^{13}CH_3; R^2\!=\!{}^{13}CD_3\}$;

(S)-2-($^2$H$_5$)ethyl-2-hydroxy-3-oxo-4-($^{13}$C)methylbutanoic acid {X$^1$=X$^2$=H; Y$^1$=Y$^2$=Y$^3$=C; R$^1$=$^{13}$CH$_3$; R$^2$=CD$_3$-CD$_2$}.

In another embodiment of the present invention, the compound of formula (I) having an (S) configuration is chosen from the group consisting of:

(S)-1,2,3-($^{13}$C)-2-(1'-$^2$H$_2$,$^{13}$C$_2$)ethyl-2-hydroxy-3-oxo-4-($^2$H$_3$)butanoic acid {X$^1$=X$^2$=H; Y$^1$=Y$^2$=Y$^3$=$^{13}$C; R$^1$=CD$_3$; R$^2$=$^{13}$CH$_3$-$^{13}$CD$_2$};

(S)-1,2,3-($^{13}$C)-2-(1'-$^2$H$_2$,2'-$^2$H, $^{13}$C$_2$)ethyl-2-hydroxy-3-oxo-4-($^2$H$_3$)butanoic acid {X$^1$=X$^2$=H; Y$^1$=Y$^2$=Y$^3$=$^{13}$C; R$^1$=CD$_3$; R$^2$=$^{13}$CH$_2$D-$^{13}$CD$_2$};

(S)-1,2,3-($^{13}$C)-2-(1'-$^2$H$_2$,2'-$^2$H$_2$,$^{13}$C$_2$)ethyl-2-hydroxy-3-oxo-4-($^2$H$_3$)butanoic acid {X$^1$=X$^2$=H; Y$^1$=Y$^2$=Y$^3$=$^{13}$C; R$^1$=CD$_3$; R$^2$=$^{13}$CHD$_2$-$^{13}$CD$_2$}.

Another object of the invention is to provide a process for preparing a compound of formula (I) having an (S) configuration, comprising:
reacting an alpha-ketoacid of formula (II)

(II)

with an alpha-ketoacid of formula (III),)

(III)

wherein X$^1$, X$^2$, Y$^1$, Y$^2$, Y$^3$, R$^1$ and R$^2$ have the meaning defined for formula (I), in the various embodiments,
in the presence of acetohydroxy acid synthase II (AHAS II), of the coenzyme thiamine pyrophosphate (TPP); the redox cofactor flavin adenine dinucleotide (FAD); magnesium salts and a buffer.

This process being enzymatic, it:
- is regioselective (the enzyme reacts preferably with certain sites of the alpha-ketoacids of formula (II) and/or (III)) and stereospecific (the 2-(S) alpha-hydroxy ketoacids are exclusively obtained);
- does not require a step of separating enantiomers;
- yields compounds of formula (I) having an (S) configuration in high yields (at least 50%),
- lowers and may in some instances eliminate the formation of byproducts; and/or
- provides high reaction rates under mild reaction conditions.

Another advantage of this enzymatic process for preparing a compound of formula (I) resides the production of labeled compounds that are not easily obtainable by the chemical syntheses described in the art.

This process may use plant, bacterial, yeast or fungal AHAS II, which may be wild types, recombinant, engineered and mutated.

In an embodiment of the invention, the acetohydroxy acid synthase II (AHAS II) is advantageously the wild type AHAS isozyme II from *Escherichia coli* (WT) prepared in Bar-Ilan et al, (Biochemistry 40 (2001) 11946-54). In another embodiment of this invention, the AHAS II is advantageously a recombinant AHAS isozyme II with a tag within an N-terminal position.

In this process, the pH of the reaction may be from 5 to 9, preferably from 6 to 7.8, including the stated values.

The reaction between alpha-ketoacids of formulae (II) and (III) is performed in the presence of a buffer. The buffer is, advantageously, chosen in a group consisting of phosphates in particular, monopotassium phosphate, dipotassium phosphate, monosodium phosphate, disodium phosphate; sodium hydrogen maleate, imidazole; 3-(N-morpholino)propanesulfonic acid (MOPS); triethanolamine (TEA); 3-[[1,3-dihydroxy-2-(hydroxymethyl)propan-2-yl]amino]-2-hydroxypropane-1-sulfonic acid (TAPSO); 2-(N-morpholino) ethanesulfonic acid (MES), 4-(2-hydroxyethyl)-1-piperazine ethanesulfonic acid (HEPES); piperazine-N,N'-bis(2-ethanesulfonic acid) (PIPES); and tris (hydroxymethyl)aminomethane (TRIS).

In this process, the concentration of the buffer in the reaction mixture may be between 0.01 M and 0.25 M, including the stated values.

The concentration of acetohydroxy acid synthase II (AHAS II) in the reaction mixture may be between 200 to 700 μg/ml, preferably between 300 and 500 μg/ml, including the stated values.

In this process, the concentration of each of alpha-ketoacid of formula (II) and the alpha-ketoacid of formula (III) is between 2 mM and 100 mM, preferably between 5 mM and 50 mM including the stated values.

In a preferred embodiment, the alpha-ketoacids of formulae (II) and (III) are present in a stoichiometric amount.

The reaction between alpha-ketoacid of formula (II) and the alpha-ketoacid of formula (III) between may be performed at a temperature between 15 and 40° C., preferably between 20 and 30° C., including the stated values.

In the process according to the present invention, the reaction between alpha-ketoacid of formula (II) and the alpha-ketoacid of formula (III) may be performed in the presence of a water-miscible organic solvent chosen from 2-propanol, dimethyl sulfoxide (DMSO), dimethyl formamide (DMF), and acetamide, in a concentration from 0 to 50% v/v.

The reaction between the alpha-ketoacid of formula (II) and the alpha-ketoacid of formula (III) may optionally be performed in the presence of a reducing agent to improve enzyme stability such as dithiothreitol (DTT); one or more buffering salts; in the total concentration from 0 to 150 mM.

Magnesium ions may be replaced by other divalent metal cations being able to activate the enzyme, such as calcium, barium, manganese, zinc, cobalt and nickel.

When added to a perdeuterated expression culture, the compounds of formula (I) are then incorporated into the target protein by the bacteria without detectable scrambling.

The invention also concerns a process for the isotopic labeling of amino acids selected from the group consisting of valine (Val), leucine (Leu) and isoleucine (Ile), and more particularly for the specific labeling of valine, leucine and isoleucine methyl groups, in proteins and biomolecular assemblies, using a compound of formula (I) having an (S) configuration according to the present invention.

This process allows an efficient and stereospecific labeling of methyl groups in isoleucine, leucine and valine amino acids in proteins and biomolecular assemblies by the addition of a compound of formula (I) having an (S) configuration according to the present invention, in the culture medium containing bacteria overexpressing a protein or proteins of interest, without detectable scrambling. The bacteria may be, but not limited to, *Escherichia coli*. The protocol used may be that described, for example, in WO 2011/083356.

The invention also concerns a process for analyzing proteins and biomolecular assemblies by NMR spectroscopy comprising a step of isotopic labeling of valine, leucine and amino acids in proteins and biomolecular assemblies to be analyzed, by a compound of formula (I) having an (S) configuration according to the invention.

Compounds of formula (I) thus enable to perform structural studies of proteins containing valine, leucine and isoleucine amino acids. The labeling with the compounds of formula (I) enables to detect weak, as low as 0.05 Hz, dipolar and scalar interactions in proteins of less than 30 kDa.

The invention further concerns a kit for the isotopic labeling of valine, leucine and isoleucine amino acids, in particular, for the isotopic labeling of valine, leucine and isoleucine methyl groups, in proteins and biomolecular assemblies, comprising one or more compounds of formula (I) having an (S) configuration according the invention.

BRIEF DESCRIPTION OF THE DRAWINGS

Other advantages and features of the present invention may be better understood with respect to the following examples given for illustrative purposes and the accompanying figures.

FIG. 3 represents the synthesis of 2-(S)-2-hydroxy,2-(2'-$^{13}$C-1'-D$_2$)-ethyl,3-oxo-4-D$_3$-butanoate (I).
Upper panel: the NMR spectra of the equimolar mixture of (U-D)-pyruvate and 4-$^{13}$C-3-D$_2$-2-oxobutanoate (left) and the 2-(S)-2-hydroxy,2-(2'-$^{13}$C-1'-D$_2$)-ethyl,3-oxo-4-D$_3$-butanoate (also referred to as precursor delta-1) after the addition of AHAS II (right) are represented. Some acetolactate (less than 10%) are formed during the reaction but are not observable as they are deuterated.
Lower panel: the synthetic scheme of 2-(S)-2-hydroxy,2-(2'-$^{13}$C-1'-D$_2$)-ethyl,3-oxo-4-D$_3$-butanoate is represented. $^{13}$C labeled carbon atoms are displayed in bold.

FIG. 4 represents the synthesis of 2-(S)-2-hydroxy,2-(D$_5$) ethyl,3-oxo,4-$^{13}$C-butanoate.
Upper panel: the NMR spectra of the equimolar mixture of (U-D)-2-oxobutanoate and 3-$^{13}$C-pyruvate (left) and the final product (2-(S)-2-hydroxy,2-(D$_5$)ethyl,3-oxo,4-$^{13}$C-butanoate) after addition of AHAS II (right) are represented. The peaks at 1.35 and 1.57 ppm correspond to the hydrated form of pyruvate (left) and those at 1.32 and 1.55 ppm to acetolactate formed during the reaction (right)
Lower panel: the synthetic scheme of 2-(S)-2-hydroxy,2-(D$_5$)ethyl,3-oxo,4-$^{13}$C-butanoate (also referred to as precursor gamma-2) is represented. $^{13}$C labeled carbon positions are displayed in bold.

FIG. 5 represents the synthesis of 2-(S)-2-hydroxy,2-($^{13}$C)methyl,3-oxo,4-$^{13}$C-butanoate.
Upper panel: the NMR spectra of the 3-$^{13}$C-pyruvate (left) and the final product (2-(S)-2-hydroxy,2-($^{13}$C)methyl,3-oxo, 4-$^{13}$C-butanoate) after addition of AHAS II (right) are represented. The peaks at 1.35 and 1.57 ppm correspond to the hydrated form of pyruvate.
Lower panel: the synthetic scheme of 2-(S)-2-hydroxy,2-($^{13}$C)methyl,3-oxo,4-$^{13}$C-butanoate (also referred to as acetolactate) is represented. $^{13}$C labeled carbon positions are displayed in bold.

FIG. 5a represents the synthesis of 2-(S)-2-hydroxy,2-($^{13}$C$_2$-1'-D$_2$)-ethyl-3-oxo-1,2,3-$^{13}$C-4-D$_3$-butanoate.
Upper panel: the NMR spectra of the equimolar mixture of (U—$^{13}$C)-3-D$_2$-2-oxobutanoate and (U-D)-2-$^{13}$C-pyruvate (left) and the final product after addition of AHAS II (right) are represented. The peaks at 1.35 and 1.57 ppm correspond to the hydrated form of pyruvate (left) and those at 1.32 and 1.55 ppm to acetolactate formed during the reaction (right). Lower panel: the synthetic scheme of the synthesis of 2-(S)-2-hydroxy,2-($^{13}$C$_2$-1'-D$_2$)-ethyl-3-oxo-1,2,3-$^{13}$C-4-D$_3$-butanoate is represented. $^{13}$C labeled carbon positions are displayed in bold.

DETAILED DESCRIPTION

Examples

Materials and Procedures

The compounds used are commercially available: CDN Isotopes Inc. for (D$_5$)-2-oxobutanoate, Sigma-Aldrich for 4-($^{13}$C)-2-oxobutanoate, 3-$^{13}$C-pyruvate, 2-$^{13}$C-pyruvate, pyruvate and Cambridge Isotopes Laboratories for U—($^{13}$C)-2-oxobutanoate. The plasmid carrying the sequences encoding the two subunits of AHAS II was kindly provided by Dr. David Chipman (Ben Gurion University of Negev).

All $^1$H and $^{13}$C one-dimensional NMR spectra were recorded on a Varian DirectDrive spectrometer operating at a proton frequency of 600 MHz equipped with a cryogenic triple resonance pulsed field gradient probe head.

The two-dimensional $^1$H-$^{13}$C HMQC of labeled protein were recorded with 1288 (/780) complex data points in direct dimension (maximum $t_2$=99 ms (/60 ms)) and 512 (/380) points in carbon dimension (maximum $t_1$=128 ms (/47 ms)).

Example 1: Preparation of l'acetohydroxyacid synthase II (AHAS II)

The overexpression and purification of AHAS II were made according to the method of Hill et al. (Biochem J. 1997). *E. coli* BL21 (DE3), carrying the plasmid of the overexpressed AHAS II, were grown at 37° C. in a Luria-Bertani medium.

When the optical density (OD) or absorbance at 600 nm reached 0.5-0.7, AHAS II expression was induced by the addition of isopropyl β-D-1-thiogalactopyranoside (IPTG) to a final concentration of 0.4 mM. Expression was performed for 12 hours at 20° C. The bacteria were harvested by centrifugation at 5000 g for 15 minutes at 4° C., resuspended in 10 ml of TRIS-HCl 0.1 M pH 7.5 and centrifuged at 4000 g for 15 minutes at 4° C. The bacteria were resuspended in 10 ml of buffer (buffer A: TRIS 50 mM pH 8, KCl 0.5 M, imidazole 10 mM and FAD 20 μM). The cells were disrupted by sonication for 2 minutes and the insoluble materials were removed by ultracentrifugation at 45,000 g for 45 minutes at 4° C.

The supernatant was then deposed on a NiNTA column (obtained from Qiagen) equilibrated with buffer A. After washing the column with 5 volumes of buffer A, the AHAS II was eluted using buffer B (buffer B: TRIS 50 mM pH 8, KCl 0.5 M, imidazole 400 mM and FAD 20 μM). The fractions containing AHAS II were pooled, concentrated, dialyzed against deionized and lyophilized. The activity of AHAS II was determined by measuring the decrease of absorbance of pyruvate at 333 nm.

Example 2: Synthesis of $^{13}$C and $^2$H (D) labeled 2-(S)-2-hydroxy,2-ethyl,3-oxo,4-butanoate and 2-(S)-2-hydroxy,2-methyl,3-oxo,4-butanoate The synthesis two compounds according to the invention: 2-(S)-2-hydroxy,2-ethyl,3-oxo,4-butanoate and 2-(S)-2-hydroxy,2-methyl,3-oxo,4-butanoate labeled with D and $^{13}$C, was performed according to the protocol described by D. Chipman for the chiral synthesis of aromatic alpha-hydroxy ketones (Biotechnol Bioeng. 2004 88(7):825-31 and US 2006/0148042).

Figure 1:
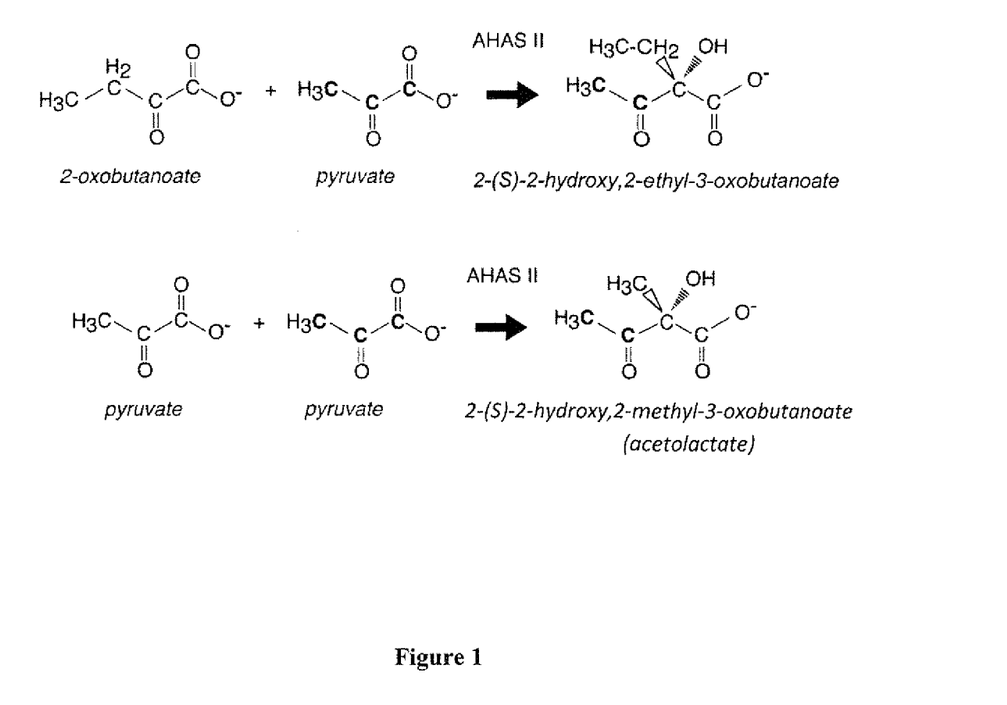
FIG. 1 represents the enzymatic synthesis of 2-(S)-2-hydroxy,2-ethyl,3-oxobutanoate and 2-(S)-2-hydroxy,2-methyl,3-oxobutanoate (also referred to as precursors) by acetohydroxyacid synthase II (ASAH II) of *E. coli*. The carbon atoms of the final compound originating from one of the pyruvate molecules are shown in bold.
Figure 2:
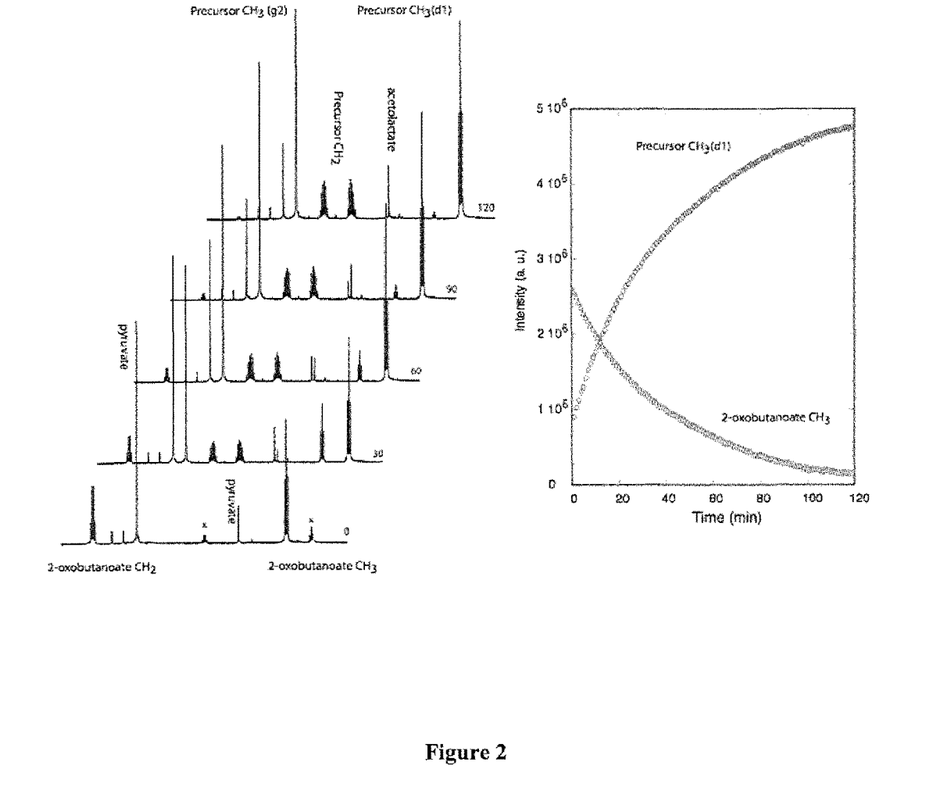
FIG. 2 represents the enzymatic synthesis of 2-(S)-2-hydroxy,2-ethyl,3-oxobutanoate (also referred to as precursor). Left: one-dimensional NMR spectra of a 1/1 mixture of oxobutanoate/pyruvate in presence of AHAS II as a function of time is represented. Right: the evolution as a function of time of the resonance intensity of the methyl of group of oxobutanoate and the methyl group in position delta-1 of the precursor is represented.

Synthesis of the $^{13}$C and $^2$H labeled compounds was made by adding an aliquot of AHAS II, purified as described above, in an equimolar mixture of $^{13}$C and $^2$H (D) labeled pyruvate and 2-oxobutanoate. The reaction was monitored by $^1$H NMR spectra (one-dimensional) and condensation of pyruvate with 2-oxobutanoate was completed after 2 hours as shown in FIG. 2. A large number of compounds of formula (I) can be synthesized enzymatically using reagents differently labeled by $^{13}$C and $^2$H.

A. Synthesis of 2-(S)-2-hydroxy,2-(2'-$^{13}$C-1'-D$_2$)-ethyl,3-oxo-4-D$_3$-butanoate (precursor delta-1)

33 mM of (U-D)-pyruvate (perdeuterated by treatment of unlabeled pyruvate in D$_2$O at pH 10.7 for 72 hours) was mixed with 33 mM of 4-$^{13}$C,3-D$_2$-2-oxobutanoate in 3 ml of D$_2$O buffer potassium phosphate 50 mM pH 7.8, MgCl$_2$ 10 mM, Thiamine diphosphate 1 mM, FAD 20 mM.

Figure 3:
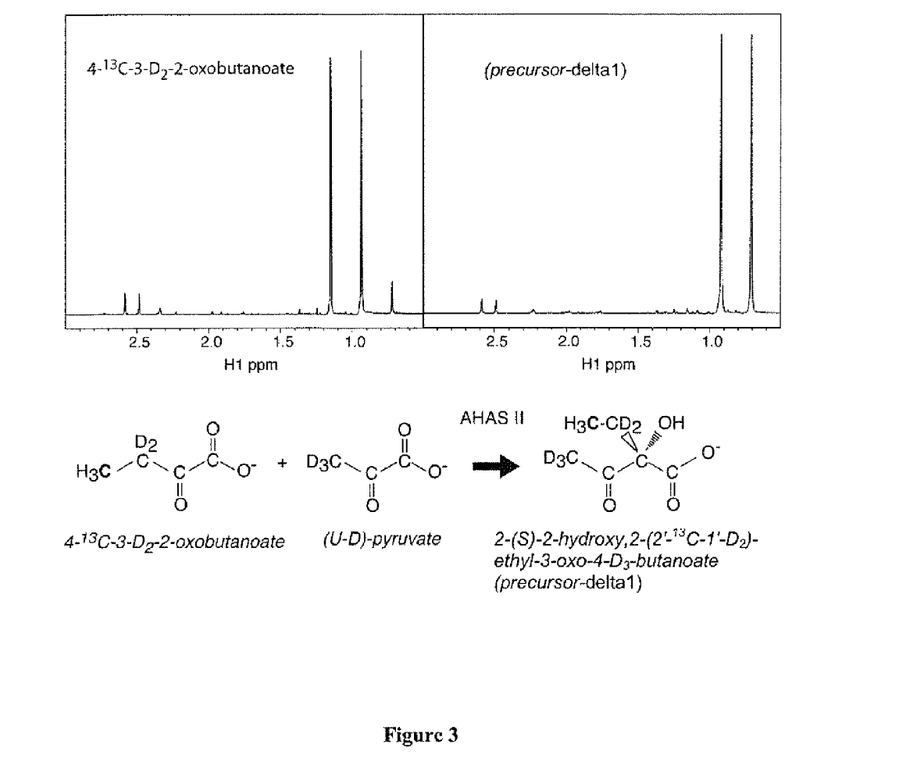

The reaction was initiated by the addition of 6 mM (420 mg/ml) of AHAS II and followed by $^1$H NMR (one-dimensional). $^1$H NMR Spectra of initial and final compounds are represented in FIG. 3.

B. Synthesis of 2-(S)-2-hydroxy,2-(D$_5$)ethyl,3-oxo, 4-$^{13}$C-butanoate (precursor gamma-2)

33 mM of 3-$^{13}$C-Pyruvate was mixed with the same concentration of D$_5$-2-oxobutanoate in 3 ml of D$_2$O buffer potassium phosphate 50 mM pH 7.8, MgCl$_2$ 10 mM, Thiamine diphosphate 1 mM, FAD 20 mM.

Figure 4:
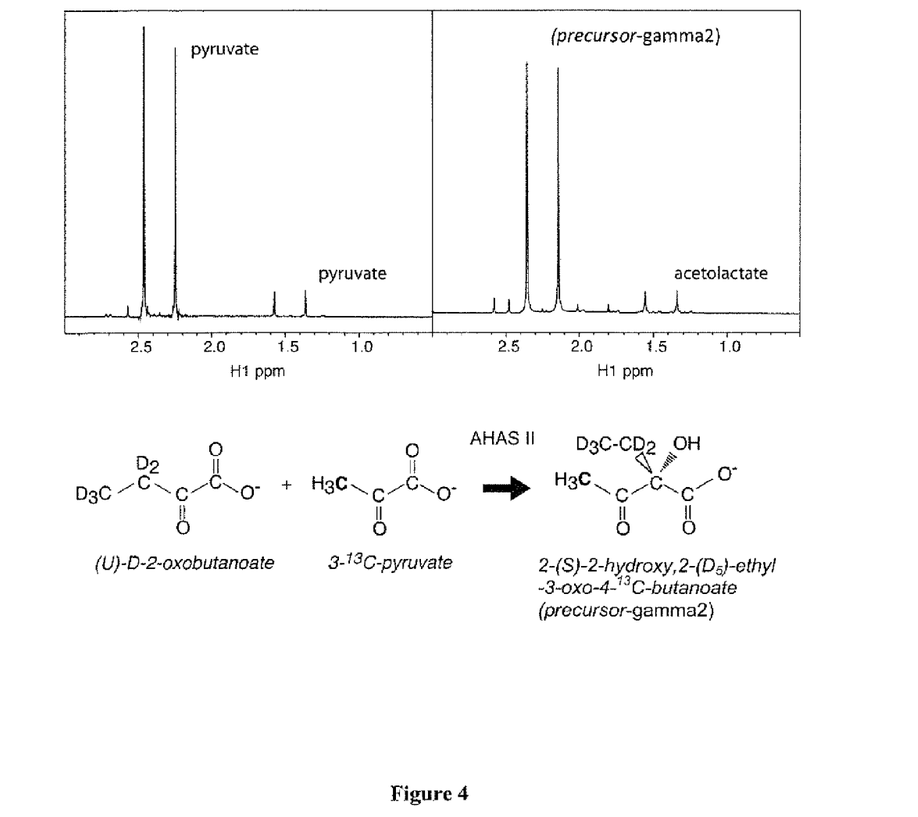

The reaction was initiated by the addition of at 6 mM (420 mg/ml) of AHAS II and followed by $^1$H NMR (one-dimensional). $^1$H NMR Spectra of initial and final compounds are presented in FIG. 4.

C. Synthesis of 2-(S)-2-hydroxy,2-($^{13}$C)methyl,3-oxo,4-($^{13}$CD$_3$)-butanoate (acetolactate)

66 mM of 3-$^{13}$C-pyruvate was dissolved in 3 ml of D$_2$O buffer potassium phosphate 50 mM pH 7.8, MgCl$_2$ 10 mM, Thiamine diphosphate 1 mM, FAD 20 mM.

Figure 5:
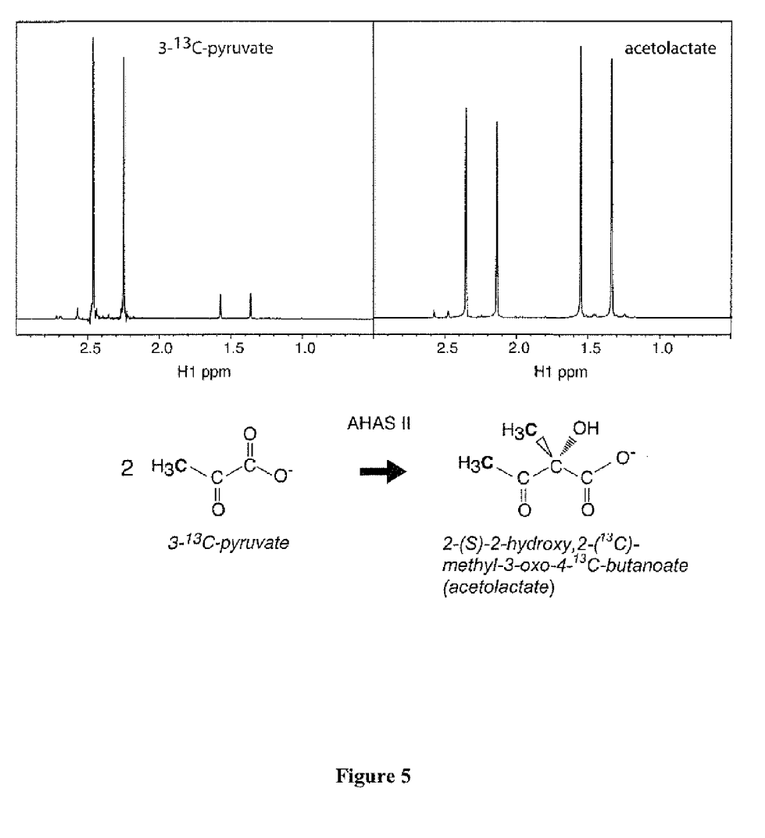

The reaction was initiated by the addition of 6 mM (420 mg/ml) of AHAS II and followed by $^1$H NMR (one-dimensional). $^1$H NMR spectra of pyruvate and final compound (2-(S)-2-hydroxy,2-($^{13}$C)methyl,3-oxo,4-($^{13}$CD$_3$)-butanoate) are presented in FIG. 5. Deuteration at position 4 is accomplished by $^1$H/$^2$H(D) exchange as described by P. Gans et al. (Angew. Chem. Int. Ed., 2010, 49, pages 1958-1962).

D. Synthesis of 2-(S)-2-hydroxy,2-($^{13}$C$_2$-1'-D$_2$)-ethyl-3-oxo-1,2,3-$^{13}$C-4-D$_3$-butanoate 33 mM of U-D, 2-$^{13}$C-Pyruvate was mixed with U—$^{13}$C, 3-D$_2$-2-oxobutanoate at the same concentration in 3 ml of D$_2$O buffer potassium phosphate 50 mM pH 7.8, MgCl$_2$ 10 mM, Thiamine diphosphate 1 mM, FAD 20 mM.

Figure 5A:
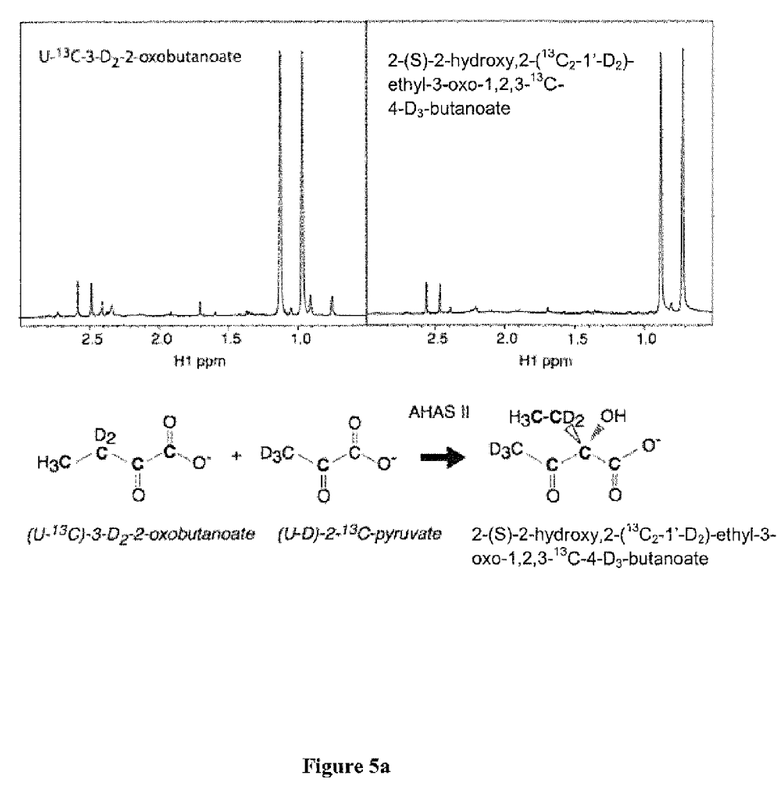

The reaction was initiated by the addition of 6 mM (420 mg/ml) of AHAS II and followed by $^1$H NMR (one-dimensional). $^1$H NMR Spectra of initial and final compounds are presented in FIG. 5a.

Example 3: Optimization of the Incorporation of (S)-2-hydroxy-2-ethyl-3-oxobutanoate in Overexpressed Protein Initial experiments to determine the level of (S)-2-hydroxy-2-ethyl-3-oxobutanoate incorporation into overexpressed proteins were performed using ubiquitin as a model system.

*E. coli* BL21(DE3) cells were transformed with a pET41c plasmid (obtained from Novagen) carrying the human His-tagged ubiquitin gene (pET41c-His-Ubi) and transformants were grown in M9/D$_2$O media containing 1 g/L of $^{15}$ND$_4$Cl and 2 g/L of U—[$^2$H]-glucose.

When the optical density or absorbance at 600 nm reached 0.8, a solution containing labeled 2-hydroxy-2-ethyl-3-oxobutanoate was added. After an additional 1 hour, ubiquitin expression was induced by the addition of β-D-1-thiogalactopyranoside (IPTG) to a final concentration of 1 mM. Induction was performed for 3 hours at 37° C. Ubiquitin was purified by Ni-NTA (obtained from Qiagen) chromatography column in a single step.

The optimal quantity of 2-hydroxy-2-ethyl-3-oxobutanoate required to achieve almost complete incorporation in the overexpressed protein was assessed in a series of cultures (100 mL each) in which different amounts of labeled precursor were added 1 hour prior induction, to final concentrations of 15, 30, 60, 80 and 100 mg/L together with 200 mg/mL U—[$^{13}$C]-methionine. The level of incorporation into the purified protein was monitored by $^{13}$C-HSQC NMR. The quantification was performed by comparing the integral of signals corresponding to Ile methyl groups with respect to the signals of the epsilon methyl groups of Met.

Figure 6:
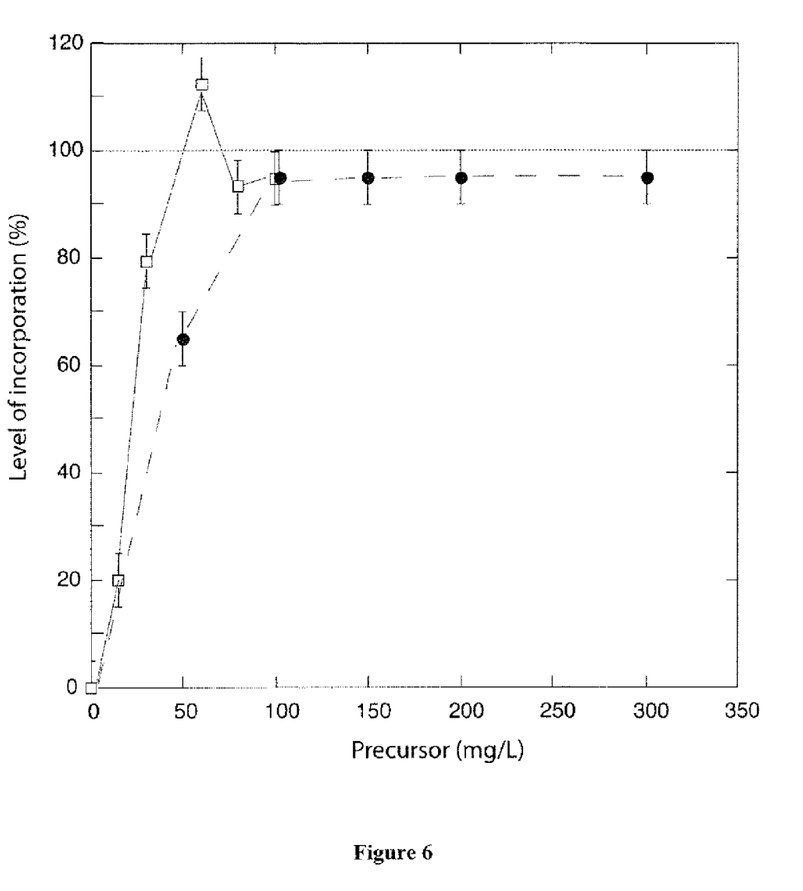
FIG. 6 represents the level of incorporation of (S)-2-hydroxy-2-ethyl-3-oxobutanoate in overexpressed proteins as a function of the amount of exogeneous precursor added. Ubiquitin was expressed in *E. coli* in M9/D$_2$O culture medium with 2 g/L of U—[$^2$H]-glucose. The level of incorporation of (S)-2-hydroxy-2-ethyl-3-oxobutanoate (squares) is compared to those (black circles) of racemic 2-hydroxy-2-[$^2$H5]ethyl-[1,2,3,4-$^{13}$C4]-3-oxobutanoate obtained by chemical synthesis (Ayala et al, 2012, Chem Commun, 48(10):1434-6.). Quantification was performed by comparing the intensities of signals corresponding to isoleucine gamma-2 methyl groups with respect to signals of the epsilon methyl groups of methionine. A level of incorporation in Ile side chains of 95% is obtained by adding about 50 mg of (S)-2-hydroxy-2-ethyl-3-oxobutanoate per liter of M9/D$_2$O culture medium compared to more than 100 mg per liter for the chemically synthetised precursor

The addition of about 50 mg of pure (S)-2-hydroxy-2-ethyl-3-oxobutanoate per liter of M9/D$_2$O culture medium achieves an incorporation level of 95% in Ile side chains (FIG. 6).

Example 4: Production of U—[$^2$H], U—[$^{15}$N], Ile-d1-[$^{13}$C$^1$H$_3$] proteins

*E. coli* BL21(DE3) cells, transformed with a pET41c plasmid carrying the human His-tagged ubiquitin gene (pET41c-His-Ubi), were progressively adapted, in three stages, over 24 hours, to a M9/D$_2$O medium containing 1 g/L $^{15}$ND$_4$Cl and 2 g/L D-glucose-d$_7$ (obtained from Isotec). In the final culture, the bacteria were grown at 37° C. in a M9 medium prepared with 99.85% D$_2$O (obtained from Eurisotop).

When the optical density or absorbance at 600 nm reached 0.8, a solution containing (S)-2-hydroxy,2-[2'-$^{13}$C,1'-D$_2$]ethyl,[4-D$_3$]-3-oxo-butanoate (prepared according to the protocol described in example 2-A) and 2-oxoisovalerate-d$_7$ was added to the culture medium to a final concentration of 65 mg/L and 200 mg/L, respectively. 1 hour later, ubiquitin expression was induced by the addition of isopropyl β-D-1-thiogalactopyranoside (IPTG) to a final concentration of 1 mM. Expression was performed for 3 hours at 37° C. before harvesting. Ubiquitin was purified by Ni-NTA (obtained from Qiagen) column chromatography in a single step.

$^{13}$C spectra were recorded at 37° C. in D$_2$O on a NMR spectrometer operating at a proton frequency of 600 MHz. Only signals for delta-1 isoleucine methyl carbons were observed in $^{13}$C spectra indicating that $^{13}$C$^1$H$_3$ groups of (S)-2-hydroxy,2-[2-$^{13}$C,1-D$_2$]ethyl,[4-D$_3$]-3-oxo-butanoate were not incorporated in the metabolic pathways of other amino acids. The incorporation level of $^{13}$CH$_3$ groups in the delta-1 position of the isoleucine amino acids was estimated to be higher than 95% based on the integration NMR signals observed in a two-dimensional $^1$H—$^{13}$C HMQC of labeled the protein.

Example 5: Production of U—[$^2$H], U—[$^5$N], Ile-g2-[$^{13}$C$^1$H$_3$] proteins

*E. coli* BL21(DE3) cells, transformed with a pET41c plasmid carrying the human His-tagged ubiquitin gene (pET41c-His-Ubi), were progressively adapted, in three stages, over 24 hours, to a M9/D$_2$O medium containing 1 g/L $^{15}$ND$_4$Cl and 2 g/L D-glucose-d$_7$ (obtained from Isotec). In the final culture, the bacteria were grown at 37° C. in a M9 medium prepared with 99.85% D$_2$O (obtained from. Eurisotop).

When the optical density or absorbance at 600 nm reached 0.8, a solution containing (2-(S)-2-hydroxy,2-(D$_5$)ethyl,3-oxo,4-$^{13}$C-butanoate (prepared according to the protocol described in example 2-B) and 2-oxoisovalerate-d$_7$ was added to the culture medium to a final concentration of 65 mg/L and 200 mg/L respectively. 1 hour later, ubiquitin expression was induced by the addition of isopropyl β-D-1-thiogalactopyranoside (IPTG) to a final concentration of 1 mM. Expression was performed for 3 hours at 37° C. before harvesting. Ubiquitin was purified by Ni-NTA (obtained from Qiagen) column chromatography in a single step.

$^{13}$C spectra were recorded at 37° C. in D$_2$O on a NMR spectrometer operating at a proton frequency of 600 MHz. Only signals for the gamma-2 methyl carbons of isoleucine were observed in $^{13}$C spectra, indicating that $^{13}$C$^1$H$_3$ groups of 2-(S)-2-hydroxy,2-(D$_5$)ethyl,3-oxo,4-$^{13}$C-butanoate were not incorporated in metabolic pathways of other amino acids. The incorporation level of $^{13}$CH$_3$ groups in the gamma-2 position of isoleucine was estimated to be higher than 95% based on the integration NMR signals observed in a two-dimensional $^1$H—$^{13}$C HMQC of labeled protein.

Example 6: Production of U—[$^2$H], U—[$^{15}$N], Ala-beta[$^{13}$C$^1$H], Ile-delta-1-[$^{13}$C$^1$H$_3$] proteins using the protocol of Godoy-Ruiz et al. (J. Am. Chem. Soc. 2010, 132, pages 1834048350)

*E. coli* BL21(DE3) cells, transformed with a pET41c plasmid carrying the human His-tagged ubiquitin gene (pET41c-His-Ubi), were progressively adapted, in three stages, over 24 hours, to a M9/D$_2$O medium containing 1 g/L $^{15}$ND$_4$Cl and 2 g/L D-glucose-d$_7$ (obtained from Isotec). In the final culture, the bacteria were grown at 37° C. in M9 media prepared with 99.85% D$_2$O (obtained from Eurisotop), 2.5 g/L of succinate-d$_5$ (obtained from Isotec).

When the optical density or absorbance at 600 nm reached 0.8, a solution containing $^{13}$CH$_3$-alanine, 4-$^{13}$C-2-ketobutyrate and 2-ketoisovalerate-d$_7$ were added to the culture medium to a final concentration of respectively 800, 75 and 200 mg/L. Note that to simplify spectra and avoid overlap, 4-$^{13}$C,3-methyl($^2$H$_3$)-2-ketoisovalerate from original protocol was substituted by perdeuterated forms of the precursors. 1 hour later, ubiquitin expression was induced by the addition of isopropyl β-D-1-thiogalactopyranoside (IPTG) to a final concentration of 1 mM. Expression was performed for 3 hours at 37° C. before harvesting. Ubiquitin was purified by Ni-NTA (obtained from Qiagen) column chromatography in a single step.

Figure 7:
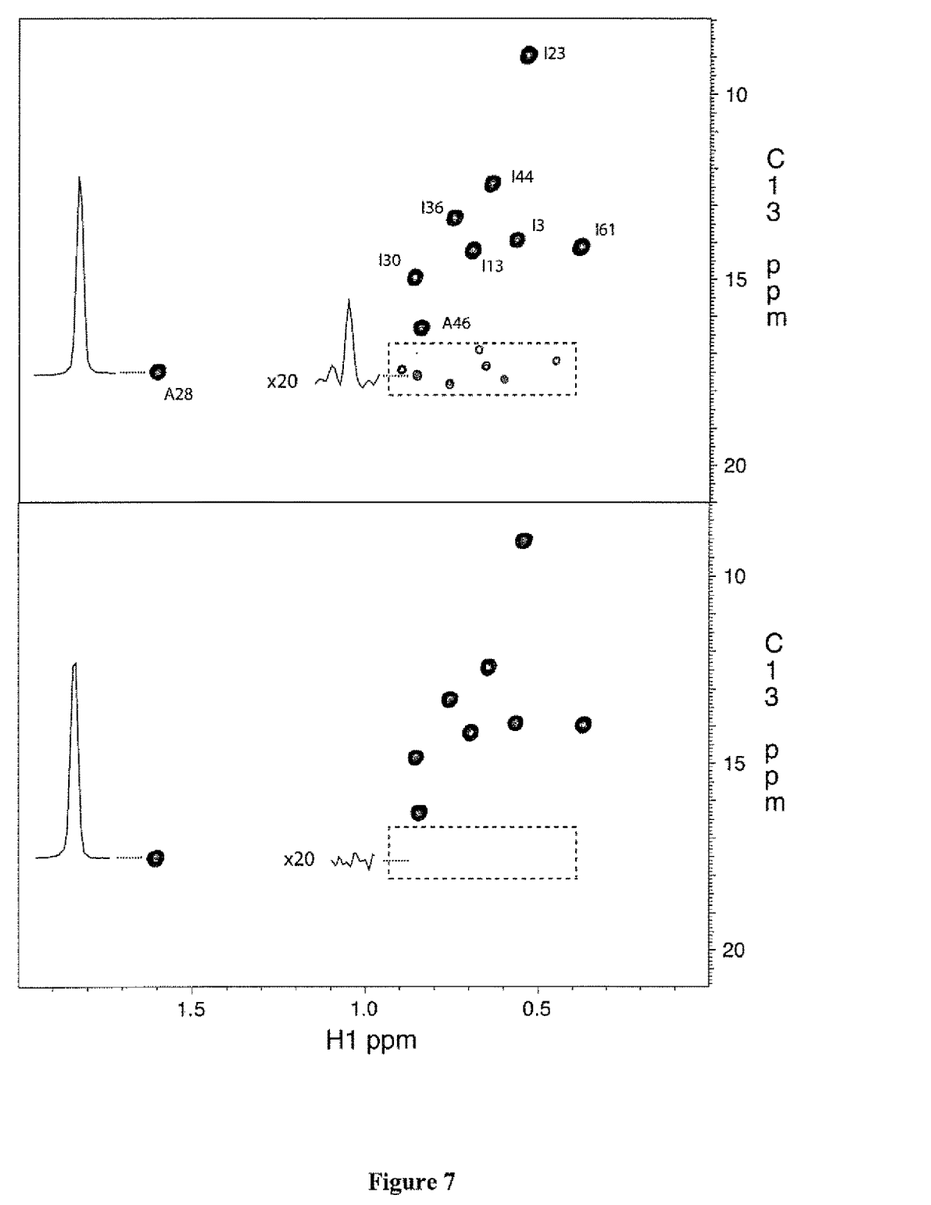
FIG. 7 represents the $^{13}$C-HSQC spectra of ubiquitin produced in *E. coli* either in the presence of labeled alanine and 2-oxobutanoate (upper panel) or in the presence of labeled alanine and the precursor synthetized using the protocol described above (lower panel). The spectra are plotted at 10% of the maximal intensity of the resonances of isoleucine amino acids except within the dotted area where the spectra are plotted at 1%. Using the protocol of Godoy-Ruiz R. et al. (J. Am. Chem. Soc., 2010, 132(51), p. 18340-50) leads to an artifactual labeling of the gamma-2 methyl group of isoleucine of 1.5-2% (upper panel), labeling which is totally suppressed when using our precursors for the culture (lower panel).
Figure 8:
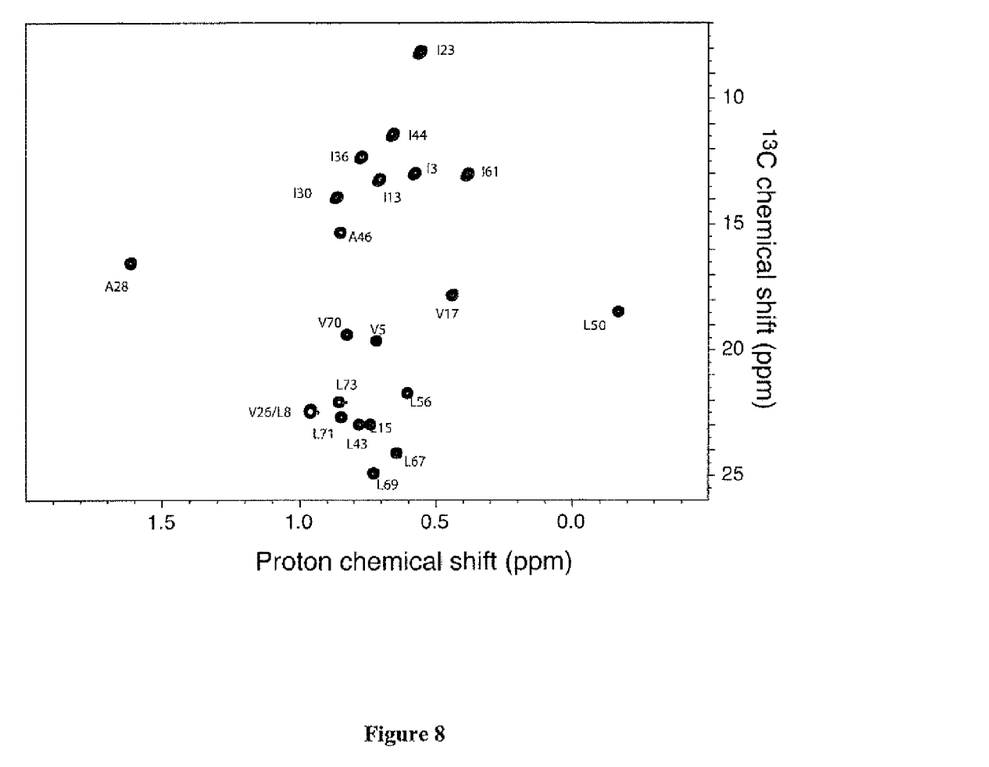
FIG. 8 represents the $^{13}$C-HSQC spectrum (methyl region) of ubiquitin produced following our labeling protocol as set forth in examples. It can be observed that only proS methyl groups of leucine and valine and the delta-1 methyl groups of isoleucine amino acids are labeled. No leakage to other methyl positions is observed.

$^{13}$C spectra were recorded at 37° C. in D$_2$O on a NMR spectrometer operating at a proton frequency of 600 MHz. Signals for alanine and delta-1 methyl carbons of isoleucine were observed in $^{13}$C spectra, but also spurious peaks corresponding to the resonance gamma-2 methyl carbons of isoleucine were observed. The level of isotopic scrambling in gamma-2 methyl carbons of isoleucine was estimated to be 1.5-2% as shown in FIG. 7. The incorporation level of $^{13}$CH$_3$ groups in the delta-1 position of isoleucine and beta position of alanine was estimated to be higher than 95% based on the integration NMR signals observed in a two-dimensional $^1$H—$^{13}$C HMQC of labeled protein.

Example 7: Production of U—[²H], U—[¹⁵N], Ala-beta[¹³C¹H₃], Ile-delta-1-[¹³C¹H₃], Leu/Val-[¹³C¹H₃] pro S proteins E. coli BL21(DE3) cells, transformed with a pET41c plasmid carrying the human His-tagged ubiquitin gene (pET41c-His-Ubi), were progressively adapted, in three stages, over 24 hours, to a M9/D₂O medium containing 1 g/L ¹⁵ND₄Cl and 2 g/L D-glucose-d₇ (obtained from Isotec). In the final culture, the bacteria were grown at 37° C. in a M9 medium prepared with 99.85% D₂O (obtained from Eurisotop).

When the optical density or absorbance at 600 nm reached 0.8, a solution containing ¹³CH₃-alanine, 2-(S)-2-hydroxy, 2-(2'-¹³C-1'-D₂)-ethyl,3-oxo-4-D₃-butanoate and 2-hydroxy,2-(¹³C)methyl,3-oxo,4-(¹³CD₃)-butanoate precursors was added to the culture medium to a final concentration of respectively 800 mg/L, 65 mg/L, 400 mg/L.

When using 2-(S)-2-hydroxy,2-(¹³C)methyl,3-oxo,4-(¹³CD₃)-butanoate precursor (prepared enzymatically as described in example 2-C) the amount of the last compound can be reduced to 200 mg/L instead of 400 mg/L. 1 hour later, ubiquitin expression was induced by the addition of isopropyl β-D-1-thiogalactopyranoside (IPTG) to a final concentration of 1 mM. Expression was performed for 3 hours at 37° C. before harvesting. Ubiquitin was purified by Ni-NTA (obtained from Qiagen) column chromatography in a single step.

¹³C spectra were recorded at 37° C. in D₂O on a NMR spectrometer operating at a proton frequency of 600 MHz. Signals for Ala, Ile-delta-1, Leu/Val-proS methyl carbons were observed in ¹³C spectra, without detectable spurious peaks corresponding to resonance of the gamma-2 of isoleucine methyl carbons. The incorporation level of ¹³CH₃ groups in the gamma-2 position of isoleucine, Leu/Val-proS and the beta position of Ala was estimated to be higher than 95% based on the integration NMR signals observed in a two-dimensional ¹H—¹³C HMQC of labeled proteins.

It is thus clear that using the protocols described above suppresses the artifacts of labeling, i.e. the residual labeling of the gamma-2 methyl groups of isoleucine that impedes collecting required data for structural determination (NOE), as illustrated in FIG. 7.

The invention claimed is:

1. A composition consisting essentially of a compound of formula (I) having an (S) configuration:

(I)

wherein
X¹ and X² are, independently from each other, ¹H (H) or ²H (D);

Y¹, Y² and Y³ are, independently from each other, ¹²C (C) or ¹³C;
R¹ is a methyl group in which the carbon atom is ¹²C (C) or ¹³C and the hydrogen atoms are, independently from each other, ¹H (H) or ²H (D);
R² is a methyl group in which the carbon atom is ¹²C (C) or ¹³C and the hydrogen atoms are, independently from each other, ¹H (H) or ²H (D); or
R² is an ethyl group in which the carbon atoms are, independently from each other, ¹²C (C) or ¹³C and the hydrogen atoms are, independently from each other, ¹H (H) or ²H (D),
with the proviso that in compound of formula (I), at the same time, at least one hydrogen atom is ²H (D) and at least one carbon atom is ¹³C.

2. The composition of claim 1, wherein in the compound of formula (I)
R¹ is chosen from a group consisting of CD₃, ¹³CH₃, ¹³CH₂D and ¹³CHD₂;
R² is a methyl group chosen from a group consisting of ¹³CD₃; or
R² is an ethyl group chosen from a group consisting of CD₃-CD₂, ¹³CH₃-CD₂, CH₃—¹³CD₂, ¹³CHD₂-CD₂, ¹³CHD₂-¹³CD₂, ¹³CH₂D-CD₂, ¹³CH₂D-¹³CD₂ and ¹³CH₃—¹³CD₂.

3. The composition of claim 1, wherein in the compound of formula (I) Y¹=Y²=Y³=C.

4. The composition of claim 1, wherein in the compound of formula (I) Y¹=Y²=Y³=¹³C.

5. The composition of claim 1, wherein said compound of formula (I) is chosen from the group consisting of:
(S)-2-(1'-²H2, 2'-¹³C)ethyl-2-hydroxy-3-oxo-4-(²H₃)butanoic acid {X¹=X²=H; Y¹=Y²=Y³=C; R¹=CD₃; R²=¹³CH₃—CD₂};
(S)-2-(1'-²H2, 2'-²H, 2'-¹³C)ethyl-2-hydroxy-3-oxo-4-(²H₃)butanoic acid {X¹=X²=H; Y¹=Y²=Y³=C; R¹=CD₃; R²=¹³CH₂D_CD₂};
(S)-2-(1'-²H₂, 2'-²H₂, 2'-¹³C,)ethyl-2-hydroxy-3-oxo-4-(²H₃)butanoic acid {X¹=X²=H; Y¹=Y²=Y³=C; R¹=CD₃; R²=¹³CHD₂_CD₂};
(S)-2-hydroxy-2-(²H₃,¹³C)methyl-3-oxo-4(¹³C)butanoic acid {X¹=X²=H; Y¹=Y²=Y³=C; R¹=¹³CH₃; R²=¹³CD₃};
(S)-2-(²H5)ethyl-2-hydroxy-3-oxo-4-(¹³C)methylbutanoic acid {X¹=X²=H; Y¹=Y²=Y³=C; R¹=¹³CH₃; R²=CD₃_CD₂}.

6. The composition of claim 1, wherein said compound of formula (I) is chosen from the group consisting of:
(S)-1,2,3-(¹³C)-2-(1'-²H2, ¹³C2)ethyl-2-hydroxy-3-oxo-4-(²H3)butanoic acid {X¹=X²=H; Y¹=Y²=Y³=¹³C; R¹=CD₃; R²=CH₃_¹³CD₂};
(S)-1,2,3-(¹³C)-2-(1'-²H2, 2'-²H, ¹³C₂)ethyl-2-hydroxy-3-oxo-4-(²H3)butanoic acid {X¹=X²=H; Y¹=Y²=Y³=¹³C; R¹=CD₃; R²=¹³CH₂D-¹³CD₂};
(S)-1,2,3-(¹³C)-2-(1'-²H2, 2'-²H2, ¹³C₂)ethyl-2-hydroxy-3-oxo-4-(²H₃)butanoic acid {X¹=X²=H; Y¹=Y²=Y³=¹³C; R¹=CD₃; R²=¹³CHD₂_¹³CD₂}.

* * * * *